(12) United States Patent
Leonard

(10) Patent No.: US 7,223,877 B2
(45) Date of Patent: *May 29, 2007

(54) USES OF HYDROQUINONE SUBSTITUTED POLYUNSATURATED FATTY ACIDS AS ANTIOXIDANTS

(76) Inventor: Edward C. Leonard, 5050 Poplar Ave., Suite 2032, Memphis, TN (US) 38157

( * ) Notice: Subject to any disclaimer, the term of this patent is extended or adjusted under 35 U.S.C. 154(b) by 97 days.

This patent is subject to a terminal disclaimer.

(21) Appl. No.: 10/780,052

(22) Filed: Feb. 17, 2004

(65) Prior Publication Data

US 2004/0162347 A1 Aug. 19, 2004

Related U.S. Application Data

(63) Continuation-in-part of application No. 10/301,119, filed on Nov. 21, 2002, now Pat. No. 6,713,512, which is a continuation-in-part of application No. 09/910,152, filed on Jul. 19, 2001, now Pat. No. 6,489,494.

(51) Int. Cl.
*C11B 1/00* (2006.01)
(52) U.S. Cl. ............... 554/8; 554/7; 554/12; 554/13; 554/218; 514/559; 514/547
(58) Field of Classification Search ......... 514/559, 514/547; 554/7, 8, 12, 13, 218
See application file for complete search history.

(56) References Cited

U.S. PATENT DOCUMENTS 6,713,512 B1 * 3/2004 Leonard ............... 514/559
2003/0129294 A1 * 7/2003 Barclay et al. ......... 426/607

FOREIGN PATENT DOCUMENTS

EP 1287825 * 3/2003

OTHER PUBLICATIONS

NIH New Release, Jun. 25, 2006.*
Attract, Posted May 9, 2001.*

* cited by examiner

Primary Examiner—Deborah D. Carr
(74) Attorney, Agent, or Firm—Wyatt, Tarrant & Combs, LLP

(57) ABSTRACT

This invention provides novel antioxidants comprising hydroquinone substituted polyunsaturated fatty acids. Such fatty acids can be obtained from crude *kombo* butter and are suitable for preventing oxidation of various organic materials. In particular, the invention relates to the use of these fatty acids as antioxidants in the treatment of cancer, the inhibition of proliferation of cells, in lowering levels of cholesterol both in vivo and in vitro and in the treatment of cognitive disorders, including but not limited to Alzheimer's disease.

5 Claims, 2 Drawing Sheets

USES OF HYDROQUINONE SUBSTITUTED POLYUNSATURATED FATTY ACIDS AS ANTIOXIDANTS

CROSS-REFERENCE TO RELATED APPLICATIONS

The present application is a continuation-in-part of U.S. patent application Ser. No. 10/301,119, filed Nov. 11, 2002 now U.S. Pat. No. 6,713,512, entitled "New Uses of Kombic Acid as An Anticancer and Cholesterol-Lowering Agent," by inventor Edward C. Leonard which is a continuation-in-part of patent application Ser. No. 09/910,152, filed Jul. 19, 2001, now U.S. Pat. No. 6,489,494, issued Dec. 3, 2001, entitled "New Uses of Kombic Acid as An Antioxidant", and the contents of which are incorporated by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to hydroquinone substituted polyunsaturated fatty acids. More particularly, the present invention relates to the use of hydroquinone substituted polyunsaturated fatty acids as antioxidants for treatment for a variety of diseases including cancer, and cognitive diseases including, but not limited to, Alzheimer's disease, learning disabilities, behavioral problems, and senile dementia, as well as for diseases requiring lowering cholesterol levels.

2. General Background of the Invention

Fats and oils are water-insoluble, hydrophobic substances of vegetable, land animal or marine animal origin that consist mostly of glyceryl esters of fatty acids, called triglycerides. Their structure is shown below, where $R_1$, $R_2$, and $R_3$ can be the same or different —$(CH_2)_xCH_3$ chains, with x being an even number of 4 or greater.

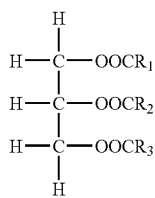

The chains (the Rs) may be completely saturated with respect to hydrogen or have one or more double bonds. When $R_1$ is seventeen carbons with no double bonds, the chain is called stearic; in this case there are thirty-five hydrogen atoms attached to the seventeen carbons. With one double bond the same carbon-length chain is called oleic and there are thirty-three attached hydrogen atoms. When there is more than one double bond, the fatty acids are polyunsaturated. Linoleic acid, for example, has eighteen carbons atoms and two double bonds, and linolenic acid has three double bonds and eighteen carbon atoms.

There are, annually, roughly 100 million metric tons of fats and oils consumed globally with about 80% used for human food. The balance is used as industrial oils; in animal feed; to make soap; and to produce oleochemicals, which have many industrial applications, most notably as plastics additives and food processing ingredients.

The principal fats and oils used in food are canola, soybean, palm, sunflower seed, coconut, palm kernel, sesame, olive, corn, cottonseed, edible tallow and lard. The most frequently occurring fatty acids found in these fats and oils are stearic ($C_{18:0}$), oleic ($C_{18:1}$), linoleic ($C_{18:1}$), linolenic ($C_{18:3}$), palmitic ($C_{16:0}$), myristic($C_{14:0}$) and lauric ($C_{12:0}$). The first two digits in the carbon subscript refer to carbon chain length, and the number after the colon refers to the number of double bonds in the chain.

Myristoleic acid, which has fourteen carbon atoms and one double bond in the chain has an ester derivative, cetyl myristoleate, with claimed efficacy in relieving the pain of rheumatoid arthritis and osteoarthritis[1,2]. The myristoleic acid used to make this product up to now has been derived from beef tallow.

There are two commonly accepted reference sources with respect to published treatises on fats and oils: "Bailey's Industrial Oil and Fat Products" and Gunstone and Padley's, "Lipid Technologies and Applications." In "Bailey's" there is the following discussion of sources of myristoleic acid, all based on land animal or marine animal origin.

9-Tetradecenoic (myristoleic) acid is the most common of the tetradecenoic acids, being first detected in whale oil in 1925 at about 1.4%, later in whale blubber oil, in shark liver oil, Antarctic whale oil, eel oil, and turtle oil. In 1924 it was suggested that myristoleic acid occurs in butterfat; it was found to constitute 1% of the total acids. It also occurs in goat milk fat, human milk fat, and various animal depot fats, (particularly beef tallow).

It is noteworthy that there is not the slightest reference in Bailey's to any vegetable oil sources.

Gunstone and Padley, in their well-recognized reference work mention hundreds of fatty acids but make no reference of any sort to myristoleic acid. Useful products can be obtained from myristoleic acid, most notably cetyl myristoleate, a possible remedy for alleviating the pain and inflammation of arthritis and related maladies[1,2]. However, cetyl myristoleate based on myristoleic acid sourced from animal origins, up to now the only ostensible source, has several disadvantages:

1) Fatty acids derived from beef tallow run the risk, albeit slight, of inducing bovine spongiform encephalitis (mad-cow disease).

2) Any fatty acid sourced from land animal or marine animal origins cannot be Kosher or the Islamic equivalent, Halal.

3) Any fatty acids sourced from land animal or marine animal origins cannot be "vegetarian" or "vegetable-oil food-grade."

Myristoleic acid, however, is not exclusively sourced from non-vegetable oil origins. There is a tree that produces a nut containing a vegetable butter that is a relatively good source of myristoleic acid[3,4,5,6]. The fat is known as *kombo butter*. It comes from the seeds of *Pycnanthus Kombo* (Myristicaceae family) found in West Central Africa. Other compounds isolated from *P. Kombo* (*P. Angolensis*) include 2'-hydroxy-4', 7-dimethoxy isoflavone and 2'-hydroxy fomonometin[8]. In addition, U.S. Pat. No. 5,674,900 00 describes the isolation and use of terpenoid quinones from the stems and leaves (not the seedfat) of *P. kombo* for use in treating diabetes[9].

The seedfat of *P. kombo* is reddish-brown and has a distinct aromatic odor. The fat also contains 20–30% of kombic acid. Kombic acid is not a fatty acid per se, rather it is a substituted fatty acid, and must be separated and removed from *kombo* butter in manufacturing downstream oleochemical products such as myristoleic acid. From *kombo* butter, the unit operations to obtain relatively pure distilled fatty acid mixtures containing appreciable levels of myristoleic acid include: 1) fat (crude *kombo* butter) saponification to split the fat and form the sodium soaps of the fatty acids, thereby separating and removing the glycerine, 2) acidulation of the sodium soaps of the fatty acids to form the free fatty acids, and 3) molecular distillation of the crude fatty acids for purposes of purification. The cetyl esters can then be formed by conventional esterification reactions. The present invention describes the unexpected isolation, and manufacture of a substituted fatty acid and substituted fatty acid derivatives from the seed fat of *Pycnanthus Kombo* (via alcohol extraction and supercritical $CO_2$ methods) and their use as antioxidants. This substituted fatty acid is kombic acid and the substituted fatty acid derivatives are derivatives of kombic acid.

Kombic Acid is not the only useful chemical isolated from *Pycnanthus Kombo*. European Patent Application EP 1 287 825 A1 and U.S. Patent Application Publication US 2003/0129294 A1 describe the isolation of Sargahydroquinoic acid (SHQA) from *Kombo* butter. Although these specific compounds have been associated with specific health benefits, it has been heretofore unrecognized that they are part of a general class of chemicals associated with these health benefits.

BRIEF SUMMARY OF THE INVENTION

The method of the present invention provides a general class of chemicals known as hydroquinone substituted polyunsaturated fatty acids as antioxidants in the treatment of cancer and cognitive diseases such as Alzheimer's, learning disabilities, behavioral problems, and senile dementia, in the stabilization of human and animal foods against rancidity, color, and odor development; and as an antioxidant for use in dietary supplements and other human and animal health formulations as well as a stabilizer in cosmetic and other personal care applications. Furthermore, the present invention provides hydroquinone substituted polyunsaturated fatty acids as cholesterol-lowering agents and anti-cancer cell proliferation agents both in vitro and in vivo.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein.

DETAILED DESCRIPTION OF THE INVENTION

Figure 1:
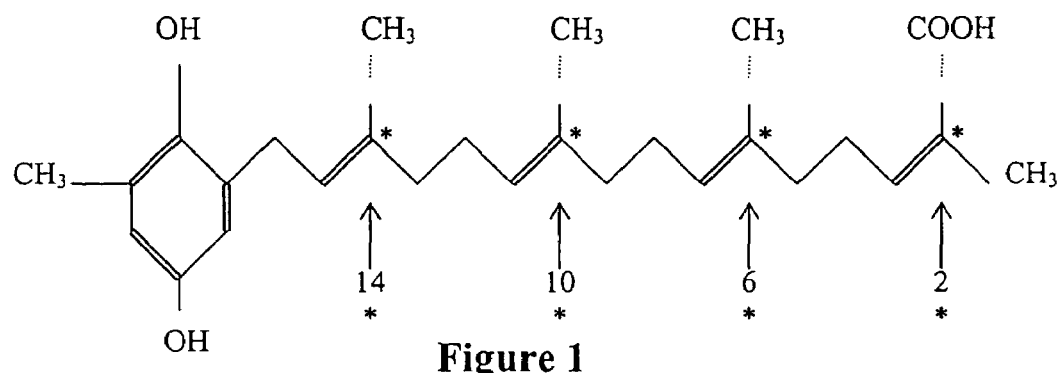
FIG. 1 shows the general chemical formula of hydroquinone substituted polyunsaturated fatty (carboxylic) acids where the carboxy (COOH) group shown at position 2, can interchange, forming individual and separate chemical entities, with methyl ($CH_3$) groups at position 6, or position 10, or position 14.

The present invention provides novel antioxidants known, in general, as hydroquinone substituted polyunsaturated fatty acids. The general structure of hydroquinone substituted polyunsaturated fatty acids is shown in FIG. 1. Two specific examples of this class of chemicals include kombic acid (FIG. 2) and Sargahydroquinoic acid (SHQA) (FIG. 3).

Kombic acid is a potent antioxidant which can be used in the treatment of cancer. Additionally, it has been shown to be useful as a cholesterol-lowering agent (U.S. patent application Ser. No. 10/301,119). Similarly, SHQA has been shown to have antioxidant properties as well[11, 12]. However, the present invention, for the first time, recognizes that it is not just these specific compounds and their derivatives that are useful in this regard. The present invention demonstrates the heretofore unrecognized fact that the general class of hydroquinone substituted polyunsaturated fatty (carboxylic) acids is useful as antioxidants.

Lipids (oils and fats; triacylglycerols), whether in the human biological system or as food products, undergo oxidation. Lipid oxidation in the human body facilitates the aging process, and in particular contributes heavily to the development of coronary artery disease. Oxidation takes place more rapidly in unsaturated fatty acids than in saturated fatty acids and most rapidly in the polyunsaturated fatty acids such as those contained (as fatty acid acylglycerols) in fish oils, linseed oil and soybean oil, inter alia.

Natural antioxidants such as the tocopherols and tocotrienols have found wide use in human and animal dietary supplements, in food products such as vegetable oils, in cosmetics, and in plastics. In each of these applications, oxidation can be a combination of autooxidation and photooxidation. Both autooxidation and photooxidation are the result of free radical, chain-propagating mechanisms that can result in cell damage and resultant ageing phenomena for animals and humans. In other applications, deleterious color, odor, and organoleptic consequences can ensue as a result of oxidation. Antioxidants can inhibit the formation and/or propagation of free radicals or promote the chain termination process and thereby shorten the propagation sequence. Antioxidants do not prevent oxidation. They serve only to extend the induction period, during which time oxidation is very slow and of no great consequence.

Antioxidant structure is critical to an organic molecule's effectiveness as an oxidation inhibitor. A polyene system, such as exists in tocotrienols and kombic acid, helps inhibit autooxidation by delocalizing odd electrons over the system. Phenolic type hydroxy groups, again occurring in both tocotrienols and kombic acid, can donate a free radical electron to terminate the propagating oxygen-bearing free radical chain. Finally, allylic C—H bonds can react with the propagatory species and act as oxidation-chain terminators. Both tocotrienols and kombic acid have several allylic C—H bonds.

The prevention of oxidation is useful for the stabilization of organic matter including, but not limited to, human dietary supplements, animal dietary supplements, edible oils, cosmetics, and plastics. The present invention comprises the use of kombic acid as such an antioxidant.

Figure 2:
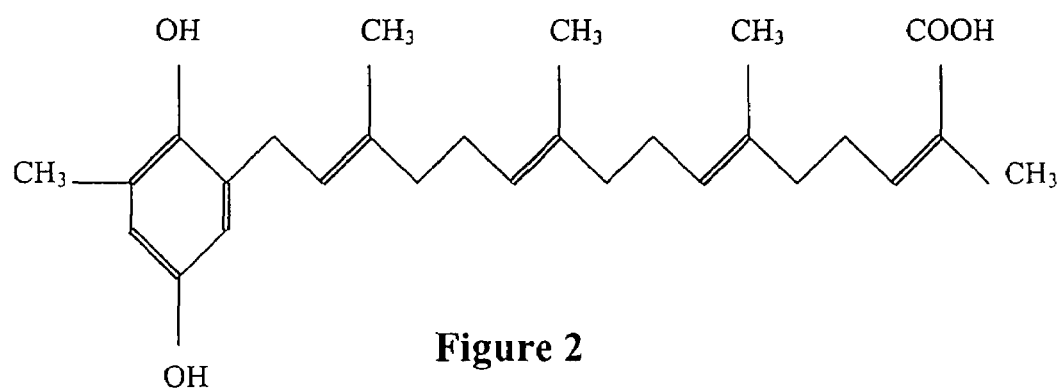
FIG. 2 shows 16(2,5-dihydroxy-3-methylphenyl-2,6,10,14-tetramethyl-2,6,10,14-hexadecatetraenoic acid (Kombic Acid)
Figure 3:
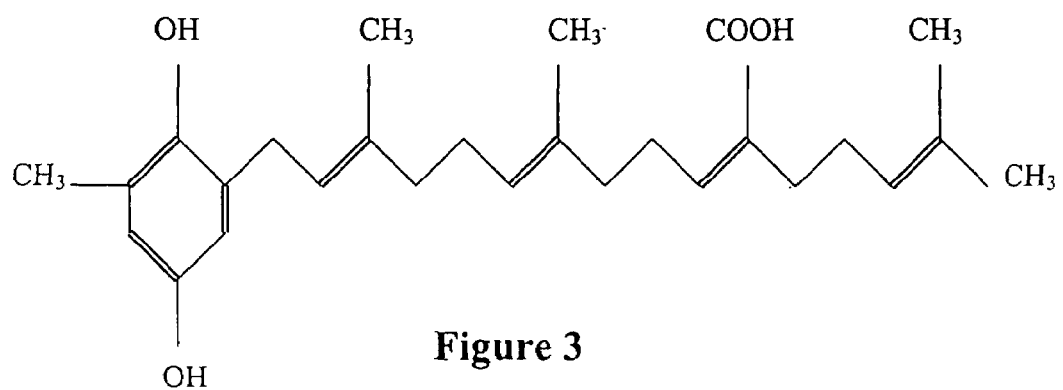
FIG. 3 shows the chemical structure of 12-(2,5-dihydroxy-3-methylphenyl)-6,10 dimethyl-2-(4-methyl-3-pentenyl)-dodecatrienoic acid (sargahydroquinoic acid) (SHQA)
Figure 4:
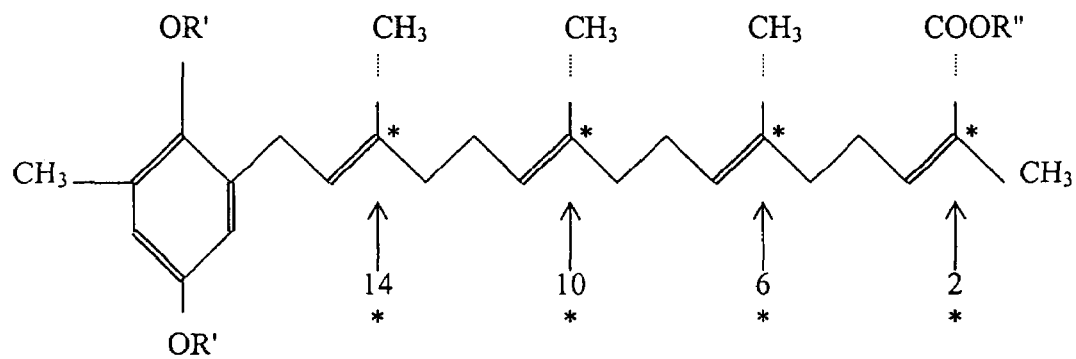
FIG. 4 shows the chemical structure of derivatives of the structure shown in FIG. 1, where R' represents an acyl group and R" represents an alkyl group.

Kombic acid is a natural terpenoid consisting of a polyisoprenoic system joined to a resorcinol nucleus with a carboxyl group at the end of the polyisoprenoic hydrocarbon chain with the structure shown in FIG. 2. The chemical name for kombic acid is 16(2,5-dihydroxy-3-methylphenyl)-2,6,10,14-tetramethyl-2,6,10,14-hexadecatetraenoic acid. The invention further provides derivatives of this structure. These derivatives are shown in FIG. 4, where R' can be acyl moieties including, but not limited to acetyl-, butyryl-, succinyl-, nicotinyl- (or hydrogen for one R') and R" can be alkyl moieties including, but not limited to methyl, ethyl and longer alkyl chains.

Figure 5:
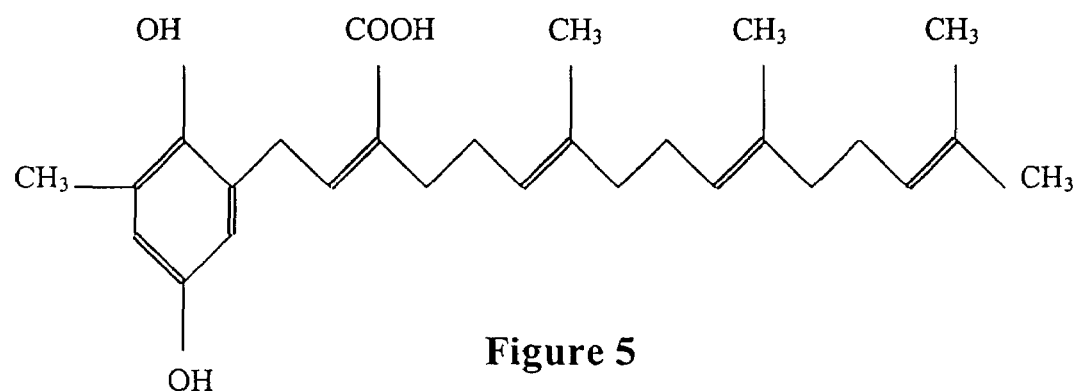
FIG. 5 shows the chemical structure of 2-[2-(2,5-dihydroxy-3-methylphenyl)ethylidene]-6,10,14-trimethyl-5,9,13-pentadecatrienoic acid.
Figure 6:
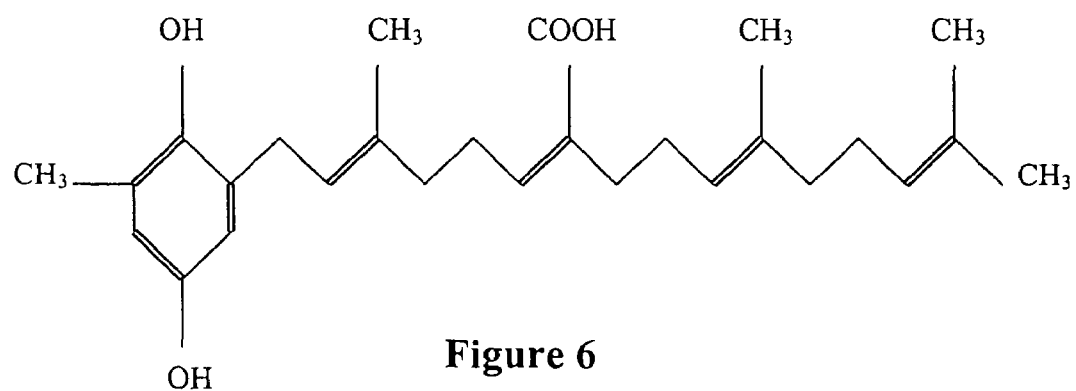
FIG. 6 shows the chemical structure of 2-[6-2,5-dihydroxy-3-methylphenyl]-4-methyl-4-hexenylidene]-6,10-dimethyl-5,9-undecadienoic acid.

The present invention teaches the use of the general class of hydroquinone substituted polyunsaturated fatty acids as antioxidants in dietary supplements, or as a vitamin-like supplement in human food and/or animal feed; as an antioxidant/stabilizer for cosmetic and personal care formulations; as stabilizers against the oxidative degradation of high polymer systems (thermoplastic and thermosetting plastics); and in the stabilization of edible oils such as soybean, sunflower seed, canola, cottonseed and others, against the development of color, odor and rancidity caused by, but not limited to, the adverse effects of heat, light, and oxygen. The general class of hydroquinone-substituted polyunsaturated fatty acids encompassed by the present invention is illustrated in FIG. 1 where the carboxy (COOH) group shown at position 2, can interchange, forming individual and separate chemical entities, with methyl ($CH_3$) groups at position 6, or position 10, or position 14. The general class of derivatives of the hydroquinone-substituted polyunsaturated fatty acids encompassed by the present invention is illustrated in FIG. 4 where R' represents an acyl group and R" represents an alkyl group. Two specific examples of chemicals encompassed by the present invention are 2-[2-(2,5-dihydroxy-3-methylphenyl)ethylidene]-6,10,14-trimethyl-5,9,13-pentadecatrienoic acid (illustrated by FIG. 5) and 2-[6-2,5-dihydroxy-3-methylphenyl]-4-methyl-4-hexenylidene]-6,10-dimethyl-5,9-undecadienoic acid (illustrated by FIG. 6)

Based on the heretofore-unrecognized similarity in structure to the tocotrienols, the present invention further teaches the use of hydroquinone substituted polyunsaturated fatty acids and their derivatives as anticancer agents inhibiting the proliferation of cells both in vivo and in vitro. Furthermore, similar to the tocotrienols, hydroquinone substituted polyunsaturated fatty acids and their derivatives are also useful as cholesterol-lowering agents.

General Methods for the Isolation of Hydroquinone-Substituted Polyunsaturated Fatty Acids The initial, crude, separation of hydroquinone-substituted polyunsaturated fatty acids is by extraction of crude *kombo* butter with aqueous sodium hydroxide or any strong base, separation of the aqueous layer which contains the sodium salt of the fatty acids, and then acidulation of the aqueous solution to reconstitute the free fatty acids. Further purification and separation of the individual fatty acids can be done by various chromatographic techniques as well as by liquid-liquid extraction and supercritical fluid extraction.

Vegetable oils have traditionally been separated from oilseeds by two methods: mechanical crushing and attendant oil expelling and solvent extraction. In the early days of solvent extraction, a variety of solvents were tested, but hexane has been the commercial solvent of choice for more than a half-century. Other solvents that have been investigated include halogenated hydrocarbons, acetone, alcohols and supercritical $CO_2$. While these other solvents can serve as oilseed extractants in place of hexane, economics, safety and yields have resulted in the choice of hexane as the standard.

The results of mechanical pressing and oil expelling and extraction by solvents is the same; the separation of saponifiable "oil" (triglycerides, diglycerides, monoglycerides and free fatty acids) from other parts of the oilseed, such as protein and fiber. Also carried along in the extraction are minor constituents that are unsaponifiable.

By conventional wisdom, kombic acid would be expected to have the same alcohol and supercritical $CO_2$ solubility as would a common fatty acid such as palmitic or myristic acid. However, the invention methods described herein indicate that this is not the case. The present invention utilizes the heretofore-unrecognized fact that kombic acid has a different alcohol and supercritical $CO_2$ solubility from the more common fatty acids and thus can be separated from them. Significantly, these invention methods are economically adaptable for commercial manufacturing. Indeed, supercritical $CO_2$ extraction is a commonly used industrial method to decaffeinate coffee. In contrast, because the prior art has not recognized that kombic acid can be extracted from *kombo* butter based on alcohol and supercritical $CO_2$ solubility differences, a chromatography procedure was used[7]; chromatography is not readily adaptable for practical, economic commercial manufacturing.

*Kombo* butter is the crude vegetable oil obtained by mechanical crushing or by hexane extraction of the seed of the *kombo* nut that is native to West Central Africa. It contains various glycerides and free fatty acids (mostly myristic and myristoleic). It also contains the substituted palmitic fatty acid known as kombic acid. Unlike palmitic acid, however, kombic acid can be separated from the other fatty acids using alcohol or supercritical $CO_2$ extraction methods. These solvents remove the conventional glycerides and fatty acids leaving the kombic acid undissolved and thus made available for conventional further isolation techniques. The following examples illustrate the purification of kombic acid from *kombo* butter.

Example 1

Purification of Kombic Acid By Liquid-Liquid Extraction

An alcohol extraction of crude *kombo* butter was made with 85% ethanol (15% water). This yielded 80+% kombic acid. The diluted alcohol was mixed with the solid *kombo* butter and agitated at ambient temperature until the butter was a fine granular solid and the alcohol layer was dark red. The alcohol was separated from the butter by filtration over sodium sulfate and the alcohol and water evaporated. Other conventional inorganic salt drying agents can also be used in place of sodium sulfate, for example, but not limited to calcium chloride. Alcohol percentage can vary from at least 70% to 100%. Methanol and isopropanol can also be used for extraction. The butter to alcohol ratio can vary from about 1:1 to at least about 1:5, with a ratio of about 1:3 being the most favorable.

Example 2

Purification of Kombic Acid By Supercritical-Fluid Extraction

A sample of alcohol-extracted *kombo* butter (76% kombic acid) was charged to an extraction vessel, and gas at selected pressure and temperature conditions was passed through the vessel for a period of time. The high pressure stream of gas plus extracted material was passed through a pressure reduction valve into a collection vessel (glass U-tube or filter flask) where the extractables precipitate. The atmospheric gas exited the U-tube and flowed through the extraction vessel, the U-tube was removed. The conditions can be changed and the procedure can be repeated to collect multiple extracts from the same initial charge, until the extractable material is depleted. Alternatively, all the extracted material can be collected in one fraction. Finally the material remaining in the extraction vessel was collected post extraction. In this particularly example there was no residual material.

The relevant weights and observations from the test are summarized below:

| | Test: Hume-1 (76% kombic acid) Charge: 7.45 g brown liquid | | |
|---|---|---|---|
| Fraction # | Wt. Collected (g) | Observations | % Kombic Acid |
| HUME-1-1 | 1.06 | Pale yellow solids | 3 |
| HUME-1-2 | 0.73 | Orange liquid | 6 |
| HUME-1-3 | 0.72 | Brown liquid | 47 |
| HUME-1-4 | 1.27 | Brown liquid | 99 |
| HUME-1-5 | 3.60 | Brown liquid | 95 |
| Sum = | 7.38 | | |
| Material balance = | 99.1% | | |

The same extraction can be carried out on crude *kombo* butter to give fractions of similar high purity with respect to kombic acid.

The purified kombic acid can then be derivatized. The kombic acid derivatives encompassed by the instant invention include, but are not limited to, a methyl ester of kombic acid, a diacetate, a dimethyl ether, a quinone and a primary alcohol, as well as those derivatives illustrated generally by FIG. 4. Such kombic acid derivatives are prepared using standard organic chemical preparative techniques known to those of skill in the art. These derivatives are usable as antioxidants either alone or in combination with kombic acid.

The following examples provide means for characterizing the purified kombic acid or kombic acid derivatives following purification and/or derivitization.

Example 3

Analytical Methods for Characterization of Kombic Acid: Gas Chromatography/Flame Ionization Detector 0.01 g of kombic acid was esterified with 1.0 ml of a mixture containing 1 part trimethylchlorosilane, 3 parts hexamethyldisilazane and 9 parts pyridine for a reaction time of 15 minutes at ambient temperature. The esterified sample trimethylsilicate ester was analyzed as follows using a Hewlett Packard 6890 Capillary Gas Chromatograph with Flame Ionization Detector.

Injection: 2.0 µl
Injector Temp: 275 C
Split ratio: 1:50
Detector Temp: 300 C
Flow: Constant pressure at 12PSI
Oven Temp program: Initial 240 C for 2 min.,
ramp at 10 C per min. to 270 C, and
hold for 25 min (Peak retention time at
approximately 22 min.) The purity as
determined by percent area = 81% kombic acid

Example 4

Analytical Methods for Characterization of Kombic Acid: High Performance Liquid Chromatography The High Performance Liquid Chromatography method included a direct injection (5 µl) of diluted kombic acid (0.01 g in 10.0 ml alcohol) per the following parameters. The mobile phase was 70% acetonitrile: 20% methanol: 10% buffer (0.1% phosphoric acid in water), using a UV Detector at 280 nm, and a C18 Reverse Phase Column at 40 C with flow of 0.9 ml./min. The peak retention time was approximately 3 min.

The Use of Hydroquinone Substituted Polyunsaturated Fatty Acids as Antioxidants It is not known, a priori, that a particular compound can function as an antioxidant. Indeed, in the paper discussing the original isolation of kombic acid[7], no mention of a use for kombic acid is made. Indeed, several possible uses for kombic acid have been postulated including its use as an antifungal agent against thrush[9]. It is important to note that none of the uses postulated thus far include the use of kombic acid as an antioxidant.

The instant invention is based on the heretofore-unrecognized function of hydroquinone substituted polyunsaturated fatty acids as antioxidants.

The following examples show lipid peroxidation antioxidant activity of hydroquinone substituted polyunsaturated fatty acids. They are in vitro simulations of how hydroquinone substituted polyunsaturated fatty acids would function in the human body as an antioxidant as a dietary supplement and food ingredient. These experiments use α-tocopherol (Vitamin E) as a standard. Natural vitamin E (d-α-tocopherol) has a long history of benefits in human nutrition. In addition to epidemiologic studies that suggest a benefit for high intakes of α-tocopherol, studies of supplementation in humans have clearly shown that α-tocopherol decreases lipid peroxidation, platelet aggregation, and functions as a potent cardiovascular anti-inflammatory agent. In the five large prospective clinical trials with α-tocopherol therapy, four have shown a beneficial effect in the prevention of cardiovascular end-points. Cardiovascular end-points include heart attack, and evidence of coronary artery disease from angiograms and/or EKG testing. An antioxidant superior or equivalent to vitamin E in experimental tests simulating the human biological system is a unique and valuable discovery as not many of the vast array of organic chemicals have any power as antioxidants at all.

Example 5

In Vitro Simulation of Protection of the Human System Against Oxidation by Hydroquinone Substituted Polyunsaturated Fatty Acids Using Rat Liver Microsomes Rat liver microsomes, previously incubated with or without inhibitor, were treated with ascorbic acid and ferrous sulfate to induce lipid peroxidation. The extent of lipid peroxidation was determined by the amount of malondialdehyde produced, which was determined by reaction with thiobarbituric acid.

Biological specimens contain a mixture of thiobarbituric acid reactive substances (TBARS), including lipid hydroperoxides and aldehydes, which increase as a result of oxidative stress. TBARS return to normal levels over time, depending upon the presence of antioxidants. In practice, TBARS are expressed in terms of malondialdehyde (MDA) equivalents. In this assay, an MDA standard is used to construct a standard curve against which unknown samples can be plotted. The presence of this compound is measured by fluorometry or spectrophotometry.

The results of this example would indicate that hydroquinone substituted polyunsaturated fatty acids have a very strong antioxidant activity.

Example 6

In Vitro Simulation of Protection of the Human System Against Oxidation by Hydroquinone Substituted Polyunsaturated Fatty Acids Using Human Low Density Lipoprotein Human low density lipoprotein is dialyzed, incubated with or without inhibitor, and then treated with 10 μM copper to induce lipid peroxidation for several hours. The extent of lipid peroxidation is determined by the amount of malondialdehyde produced, which is determined by reaction with thiobarbituric acid as described above.

This experiment would show that there is no significant difference in antioxidant activity between hydroquinone substituted polyunsaturated fatty acids and natural vitamin E; they are statistically equivalent in power. In addition, synthetic vitamin E (dl) is found to inhibit peroxidation equally as well as natural (d) vitamin E. Again, it should be noted that an antioxidant superior or equivalent to vitamin E in experimental tests simulating the human biological system is a unique and valuable discovery as not many of the vast array of organic chemicals have any power as antioxidants at all.

Example 7

Stabilization of Edible Oils Using Hydroquinone Substituted Polyunsaturated Fatty Acids The Oxygen Stability Index is used to measure the effectiveness of antioxidants in the stabilization of edible oils against oxidative degradation. The "Hours to end-point" indicate when a time/conductivity curve changes shape, with a sharp slope upturn at that time point. The temperature of the test, which measures conductivity of a solution into which oxidation products from the oil being tested is passed, is 110° C.

In this experiment, both hydroquinone substituted polyunsaturated fatty acids and TBHQ are effective antioxidants. However, TBHQ is a synthetic antioxidant. Because it is synthetic, the amount that can be used in food, for example to stabilize an edible oil, is limited by the FDA to 200 ppm. In contrast, hydroquinone substituted polyunsaturated fatty acids are natural antioxidants. Therefore, the FDA might approve its use in foods at a higher level than 200 ppm. This experiment shows that hydroquinone substituted polyunsaturated fatty acids are an effective antioxidant at levels that are FDA approvable.

Example 8

Stabilization of Plastics by Hydroquinone Substituted Polyunsaturated Fatty Acids Plastics can be formulated to contain an amount of a hydroquinone substituted polyunsaturated fatty acid such as, but not limited to, the class of compounds exemplified in FIGS. 1 through 6. As a control, these same plastics can be formulated without the invention compound. As a further control, these plastics can be formulated to contain a synthetic antioxidant compound, for example, but not limited to TBHQ. These plastics can then be exposed to heat, light and air oxidation. An analysis of color and odor development can then be made. Plastics formulated with the invention fatty acid will be more resistant to color and odor development than the plastics not containing the invention fatty acid. Furthermore, the plastics containing any one of the invention fatty acids will be either the same or more resistant to color and odor development than those plastics formulated with the synthetic antioxidant.

Example 9

Stabilization of Cosmetics by Hydroquinone Substituted Polyunsaturated Fatty Acids Cosmetics can be formulated to contain a specific amount of the invention fatty acid, such as, but not limited to the class of compounds exemplified in FIGS. 1 through 6. As a control, these same cosmetics can be formulated without a hydroquinone substituted polyunsaturated fatty acid. As a further control, these cosmetics can be formulated to contain a synthetic antioxidant compound, for example, but not limited to TBHQ. These cosmetics can then be exposed to heat, light and air oxidation. An analysis of color and odor development can then be made. Cosmetics formulated with a hydroquinone substituted polyunsaturated fatty acid will be more resistant to color and odor development than the plastics not containing a hydroquinone substituted polyunsaturated fatty acid. Furthermore, the cosmetics containing hydroquinone substituted polyunsaturated fatty acid will be either the same or more resistant to color and odor development than those cosmetics formulated with the synthetic antioxidant.

Example 10

Studies of Hydroquinone Substituted Polyunsaturated Fatty Acids with Experimental Animals When injected intraperitoneally into mice, hydroquinone substituted polyunsaturated fatty acids prolong the life of mice bearing tumor cells. Such mice bearing tumor cells include, but are not limited to Ehrlich carcinoma, sarcoma 180, or implanted murine carcinoma (IMC) tumors, Meth-A fibrosarcoma or other tumors.

Example 11

Effects of Hydroquinone Substituted Polyunsaturated Fatty Acids Alone and with Tamoxifen on Estrogen Receptor-Negative Cells Human cancer cells, such as, but not limited to, MDA-MB-435 estrogen receptor-negative human breast cancer cells are incubated in the presence of varying concentrations of a hydroquinone substituted polyunsaturated fatty acid. The incorporation of [$^3$H] thymidine into the DNA of the cells is measured. The hydroquinone substituted polyunsaturated fatty acids inhibit the proliferation of these cells. Hydroquinone substituted polyunsaturated fatty acids can act synergistically with tamoxifen, an estrogen antagonist, used extensively in the hormonal therapy of breast cancer.

Example 12

Effects of Hydroquinone Substituted Polyunsaturated Fatty Acids Alone and with Tamoxifen on Estrogen Receptor-Positive Cells Hydroquinone substituted polyunsaturated fatty acids can inhibit the proliferation of human breast cancer cells, such as, but not limited to, MCF-7 estrogen receptor-positive human breast cancer cells. Human breast cancer cells are incubated in the presence and absence of a variety of hydroquinone substituted polyunsaturated fatty acids individually. The $IC_{50}$ (the concentration of a specific hydroquinone substituted polyunsaturated fatty acid required to inhibit cell proliferation by 50%) is then determined. Hydroquinone substituted polyunsaturated fatty acids are similarly as effective as the tocotrienols. Hydroquinone substituted polyunsaturated fatty acids in combination with tamoxifen give lower $IC_{50}$ values than either of the compounds alone.

Example 13

Effects on the Estrogen Receptor

The effect of hydroquinone substituted polyunsaturated fatty acids on the estrogen receptor is investigated. Human cancer cells in culture, such as, but not limited to, MCF-7 cells are depleted of steroids and treated with a specific hydroquinone substituted polyunsaturated fatty acid, tocotrienols, or tamoxifen (used as a positive control) in the presence or absence of estradiol. The addition of excess estrogen does not reverse the inhibition by any of the hydroquinone substituted polyunsaturated fatty acids, or the tocotrienols. In contrast, it does reverse the inhibition by tamoxifen. These results indicate that hydroquinone substituted polyunsaturated fatty acids do not exert their antiproliferative effects by acting as antiestrogens.

Example 14

Effects on Protein Kinase C

Hydroquinone substituted polyunsaturated fatty acid are inhibitors of PKC activity. The $IC_{50}$ values for specific hydroquinone substituted polyunsaturated fatty acids are similar to the $IC_{50}$ values for TRF, alpha-tocopherol, and individual tocotrienols.

Example 15

Effects of Hydroquinone Substituted Polyunsaturated Fatty Acids on Farnesyl:Protein Transferase and Geranylgeranyl:Protein Transferase Activities PAP2 (ras-transformed NIH 3T3 mouse fibroblasts) cells are cultured and used as an enzyme source. hydroquinone substituted polyunsaturated fatty acids inhibit the proliferation of these cells.

Example 16

Hydroquinone Substituted Polyunsaturated Fatty Acids and Hypercholesterolemia Hypercholesterolemia associated with elevated LDL (low-density lipoprotein) cholesterol is a risk factor for CHD (coronary heart disease). LDL-cholesterol combined with oxidative stress can contribute to the formation and development of atherosclerotic plaques. To lower the risk of CHD, antioxidants such as hydroquinone substituted polyunsaturated fatty acids counteract LDL oxidation. Hydroquinone substituted polyunsaturated fatty acids produce cholesterol-lowering effects in animal models. Hydroquinone substituted polyunsaturated fatty acids are also effective in reducing elevated plasma levels of total and LDL cholesterol as well as plasma apolipoprotein B (apoB) concentrations in humans.

Example 17

Cholesterol-Lowering Responses of Hydroquinone Substituted Polyunsaturated Fatty Acids in Cells The apoB-lowering potential of hydroquinone substituted polyunsaturated fatty acids is evaluated in cells that secrete and catabolize lipoproteins similar to LDL, for example, but not limited to HepG2 cells. Confluent cells are preincubated in serum-free medium, which inhibits cell proliferation and stimulates biosynthesis of LDL-like lipoproteins. They are subsequently incubated in the same medium in the presence or absence of hydroquinone substituted polyunsaturated fatty acids at the range of nontoxic concentrations. For each compound, the highest nontoxic concentration is predetermined by a viability assay, such as but not limited to the 3-(4,5-dimethylthiazol-2-yl)-2,5-diphenyltetrazolium bromide (MTT) viability assay. At the end of the incubation, changes in medium concentration of apoB B are evaluated by ELISA and compared with changes induced in the absence of kombic acid or its derivatives. Hydroquinone substituted polyunsaturated fatty acids cause a dose-dependent reduction of medium apoB B.

All measurements disclosed herein are at standard temperature and pressure, at sea level on Earth, unless indicated otherwise. All materials used or intended to be used in a human being are biocompatible, unless indicated otherwise.

REFERENCES

1. Siemandi, H. The Effect of Cis-9-Cetyl Myristoleate and Adjunctive Therapy on Arthritis and Autoimmune Disease, *Townsend Letter for Doctors and Patients*, August/September 1997, 58–63.
2. Hesslink, Jr., Robert, Armstrong, III, David, Nagendran, M. V., Shreevatsan, Srinan, and Barathur, Raj, Cetylated Fatty Acids Improves Knee Function In Patients with Arthritis, *The Journal of Rheumatology* 2002, 29:8, 1708–1712.
3. Mensier, P. H. (1957) *Dictionnaire des Huiles Vegetales*. Editions Paul Lechevalier. Paris.
4. Wijs. J. J. A. (1906) *Vetten, Olieen en Wassen* Koloniaal Museum, Haarlem.
5. Atherton, D. and Meara, M. L. (1939) Chem. Ind. (London) 353.
6. Hilditch, T. P. and Williams, P. N. (1964) *The Chemical Constitution of Natural Fats*. Chapman & Hall, London.
7. Lok, C. M., Groenewegen, A., Stroink, J. B. A., and Ward, J. P. *Phytochemistry* 22(9) 1973–1976 (1983).
8. Omobuwajo, O. R., Adesanya, S. A., Babalola, G. O *Phytochemistry* 31, 1013–1014 (1992).
9. U.S. Pat. No., 5,674,900
10. Guthrie, Najla, and Kurowska, Elzbieta M. (2000) "Anticancer and Cholesterol-Lowering Activities of Tocotrienols" IN: Handbook of Nutraceuticals and Functional Foods. (R. Wildman R.E.C., eds.), CRC Press, Boca Raton Fla., pp. 269–280.
11. U.S. Patent Application Publication US 2003/0129294 A1, and
12. European Patent Application EP 1 287-825 A1

The foregoing embodiments are presented by way of example only; the scope of the present invention is to be limited only by the following claims.

What is claimed is:

1. An isolated antioxidant comprising a hydroquinone substituted polyunsaturated fatty acid that is useful in the inhibition of cell proliferation mediated by protein kinase C wherein said hydroquinone substituted polyunsaturated fatty acid comprises the chemical of the formula:

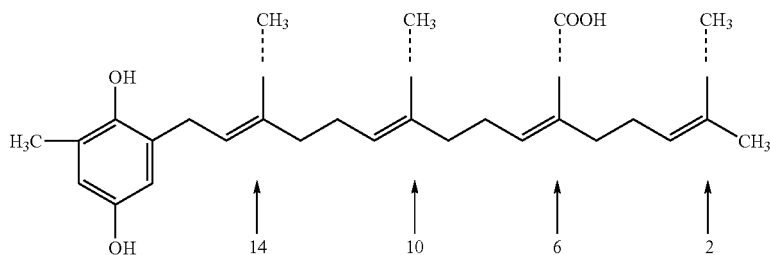

where the carboxy (COOH) group shown at position 6 can interchange, forming individual and separate chemical entities, with methyl ($CH_3$) groups at position 10, or position 14.

2. The antioxidant of claim 1, wherein said hydroquinone substituted polyunsaturated fatty acid is a derivative of said hydroquinone substituted polyunsaturated fatty acid.

3. The antioxidant of claim 2, wherein said derivative of said hydroquinone substituted polyunsaturated fatty acid comprises the chemical of the formula:

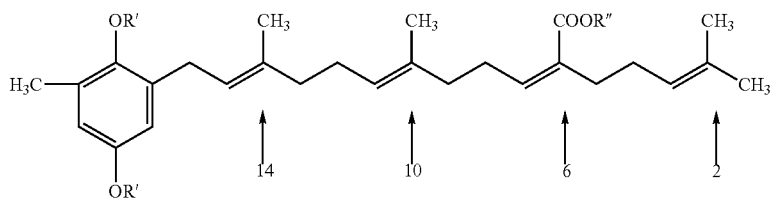

where R' represents an acyl group and R" represents an alkyl group.

4. The antioxidant of claim 2, wherein said derivative of said hydroquinone substituted polyunsaturated fatty acid comprises the chemical of the formula
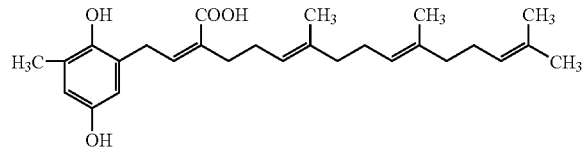
5. The antioxidant of claim 2, wherein said derivative of said hydroquinone substituted polyunsaturated fatty acid comprises the chemical of the formula
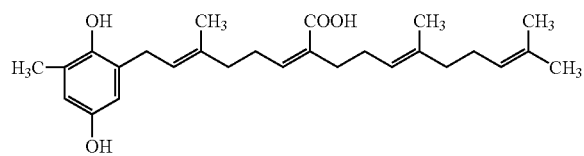
* * * * *